United States Patent [19]

Hotta et al.

[11] Patent Number: 4,568,283
[45] Date of Patent: Feb. 4, 1986

[54] MEDICAL HANDPIECE

[75] Inventors: Toshihiro Hotta, Uji; Imazatol Minoru, Otsu, both of Japan

[73] Assignee: Kabushiki Kaisha Morita Seisaksuho, Kyoto, Japan

[21] Appl. No.: 678,662

[22] Filed: Dec. 6, 1984

[30] Foreign Application Priority Data

Dec. 22, 1983 [JP] Japan .................. 58-197720[U]

[51] Int. Cl.⁴ .................................................. A61C 1/08
[52] U.S. Cl. ..................................... 433/104; 433/131
[58] Field of Search ................... 433/104, 131, 82; 310/61, 60 A

[56] References Cited

U.S. PATENT DOCUMENTS

| | | | |
|---|---|---|---|
| 1,912,586 | 6/1933 | Lysholm | 310/61 |
| 1,996,460 | 4/1935 | Coates | 310/61 |
| 3,487,546 | 1/1970 | Beierlein et al. | 433/104 |
| 4,184,256 | 1/1980 | Loge et al. | 433/104 |

FOREIGN PATENT DOCUMENTS 2613061 9/1977 Fed. Rep. of Germany ...... 433/104

Primary Examiner—John J. Wilson
Attorney, Agent, or Firm—Koda and Androlia

[57] ABSTRACT

A handpiece for medical treatment having a brushless micromotor mounted in a handpiece casing for driving a cutting tool and having a coolant passageway formed on the outer periphery of a cylindrical yoke fixed to the frame of the handpiece body. In this handpiece, the coolant passageway is formed helically around the axis of the yoke from one end to the other end of the yoke. The sectional area of the yoke in any given longitudinal sectional position along the axis of the yoke is rendered approximately equal to prevent a reduction in motor torque and also enlargement of the handpiece in diameter.

5 Claims, 10 Drawing Figures

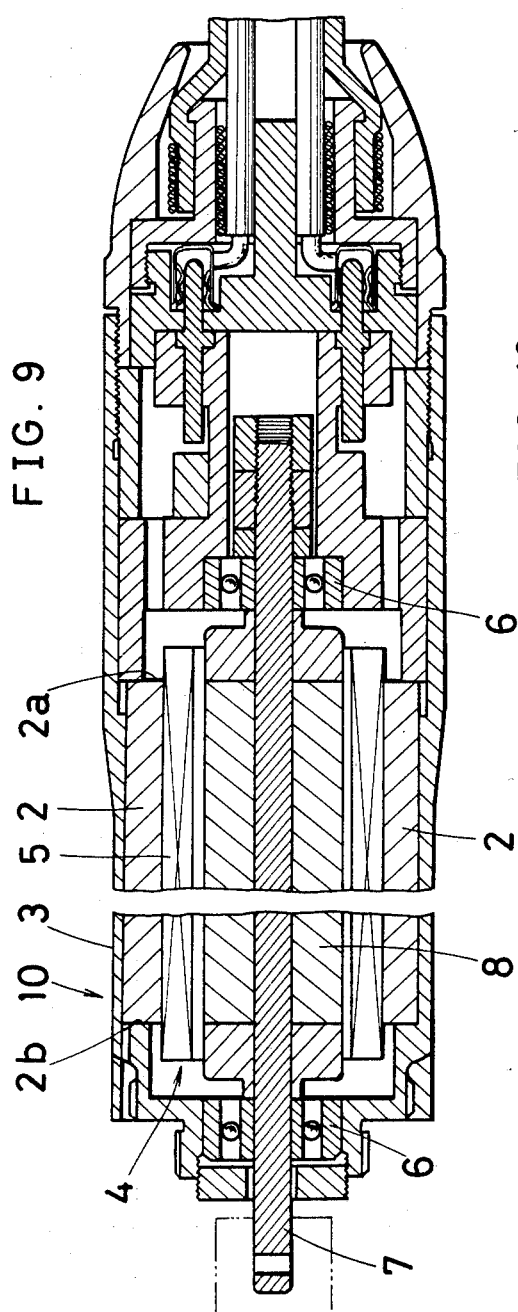
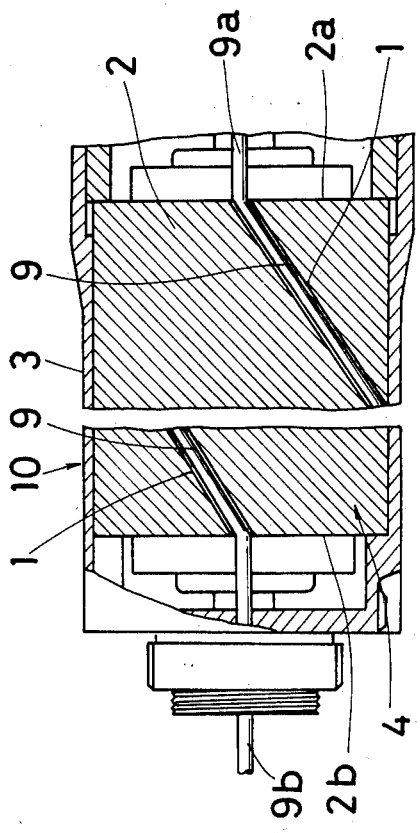
FIG. 9
FIG. 10

MEDICAL HANDPIECE

BACKGROUND OF THE INVENTION

1. Field of the Invention

This invention relates to a handpiece for use in medical treatment, especially in dental treatment, and more particularly to improvement in a dental handpiece having a brushless motor incorporated thereinto for driving a cutting tool at the end of the handpiece and having a cooling means for the teeth and the cutting tool.

2. Prior Art

A motor-driven type dental handpiece includes a cutting tool for the teeth at the end of the grip of the handpiece and is designed to drive the tool by the use of a motor incorporated into the tool and to cool both the teeth and the tool by feeding a coolant such as water or air during the cutting operation.

In the structure described above, when a coolant passageway is formed exposedly on the outside of a handpiece body, the handpiece becomes uneven in diameter throughout its length and large in size as a whole, making it uncomfortable to grip the handpiece and hence reducing operability. This is not desirable for treatment activities.

Accordingly, it is proposed to provide a coolant passageway inside the handpiece body, but this inevitably results in passing the coolant passageway through a micromotor portion, which fact produces no small effect on the magnetic path of the motor, leading to trouble such as a reduction in motor torque, production of torque ripple, etc.

As shown in a typical front view in FIG. 1, the brushless motor is generally constructed in such a manner that a necessary clearance D is formed between a coil B fixed inside a cylindrical yoke C and a motor magnet A so as to provide a magnetic path indicated by arrows in the drawing. In the motor, heretofore a coolant passageway E has been formed linearly on the outer periphery of a cylindrical yoke C and in parallel to the axis of the yoke C as shown in FIG. 2. Accordingly, the sectional area of the yoke C is largely reduced at the portion $C_1$—$C_1$ shown in an exploded view of FIG. 3 to provide a sectional area view in FIG. 4. The sectional area S of the yoke at the portion $C_1$—$C_1$ is expressed by the formula below:

$$S = (a - b_1) \times l$$

In this formula, a represent the thickness of the yoke; $b_1$ the groove thickness of coolant passageway; and l the length of the yoke. For example, if a=1.9 m/m, $b_1$=0.8 m/m and l=49 m/m, the sectional area is reduced by about 12%. Therefore, the yoke C produces a magnetic saturation phenomenon in the portion wherein the sectional area is reduced, so that the normal magnetic passageway as shown in FIG. 1 is not formed and torque is reduced. The reduction in torque results inevitably in an increase in the size of the micromotor to compensate for the amount of reduction in torque, and in turn causes an increase in the diameter of the handpiece.

When observation is made of the magnetic flux distribution during rotation of the rotor magnet A in the direction of I→II→III→IV in FIG. 5 in the micromotor having the coolant passageway formed therein, the magnetic flux distribution on the right and left with the magnet A therebetween is rendered unsymmetric at points I and III by being hindered by a coolant passageway E and is rendered symmetric at points II and Iv as is apparent from the drawing. Torque ripple is produced by such fluctuation in the magnetic flux distribution. The torque ripple thus produced deteriorates motor characteristic, constituting a direct obstacle to dental treatment.

SUMMARY OF THE INVENTION

This invention has been worked out in view of the problem above. A solution to the problem is to incorporate the brushless motor into the handpiece, form a coolant passageway in the cylindrical yoke of the motor, and form the passageway on the outer periphery of the yoke from one end to the other end of the yoke in such a manner to form the passageway helically around the axis of the yoke in order to prevent an extreme reduction in the sec-tional area of the yoke at one point of the yoke and a saturation phenomenon resulting from the reduction.

A description will now be given of a preferred embodiment of the invention with reference to the accompanying drawings.

BRIEF DESCRIPTION OF THE DRAWINGS

FIGS. 5(I) through 5(IV) are diagrammatic views showing change in magnetic flux distribution responsive to rotation of a magnet of a rotor in a conventional structure;

FIG. 9 is a longitudinal sectional view of the essential part of the handpiece showing an embodiment of the invention; and FIG. 10 is a fragmentary longitudinal sectional view of a micromotor incorporated portion showing the presence of a coolant passageway in the embodiment of FIG. 9.

DETAILED DESCRIPTION OF THE INVENTION

Figure 6:
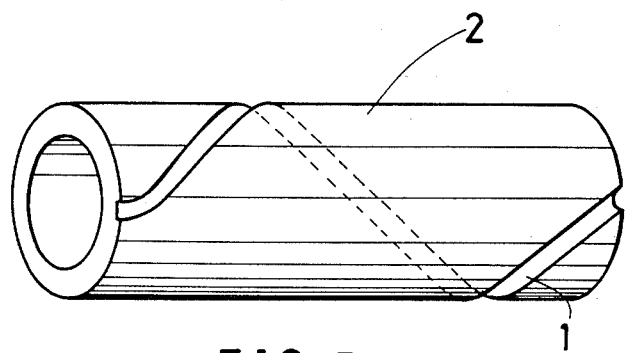
FIG. 6 is a perspective view of a yoke showing a coolant passageway of the invention.
Figure 7:
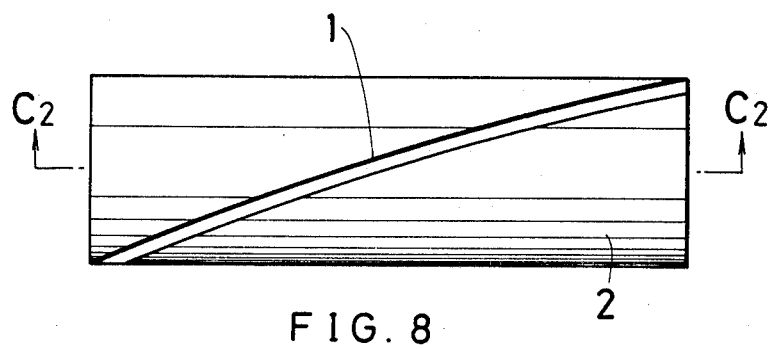
FIG. 7 is an expansion flat of FIG. 6.
Figure 8:
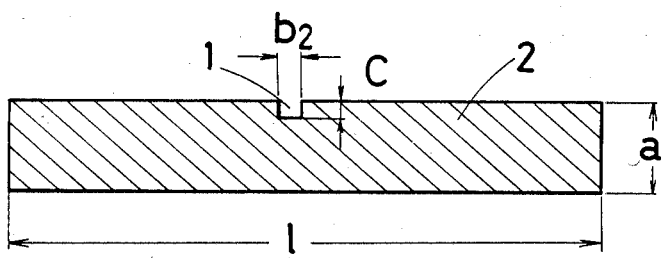
FIG. 8 is a sectional view taken in the direction of the arrow along the line C—C of FIG. 7.

FIGS. 6 through 8 show the detail of a yoke having a coolant passageway 1 of the invention formed therein. As is apparent from the drawings, the coolant passageway 1 is formed on the outer periphery of a cylindrical yoke 2 of a brushless micromotor in the invention. The passageway extends spirally around the axis of the yoke 2 from one end to the other end of the yoke 2.

In the above embodiment, the coolant passageway 1 extending from one end to the other end of the yoke has a helical groove of one turn but may have a groove of integral times as many turns. However, as is apparent from the description to be given later, it is not desirable to provide the passageway in a fractional time as many as 1.5 or 2.5 turns because there comes out imbalance in the sectional area of the yoke in any sectional position along the axis of the yoke. However, a reduction in torque, as experienced in a conventional linear coolant passageway, can be prevented. As a result, the use of the coolant passageway in the form of the above fraction-fold number of helical grooves is not objectionable.

Figure 1:
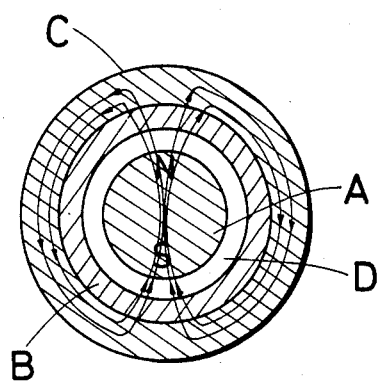
FIG. 1 is a typical front view of a brushless micromotor according to a conventional structure.
Figure 2:
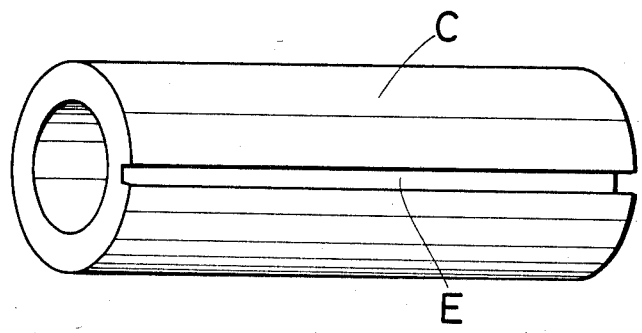
FIG. 2 is a perspective view of a yoke having a coolant passageway of a conventional structure.
Figure 3:
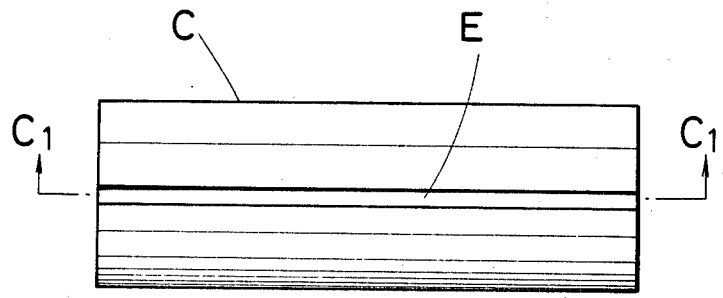
FIG. 3 is an exploded view of FIG. 2.
Figure 4:
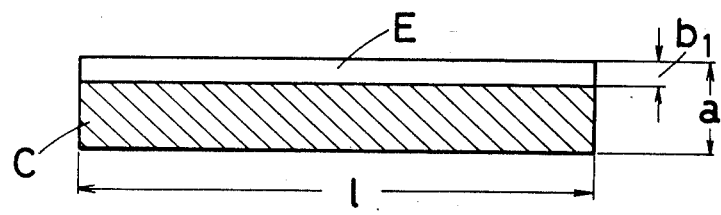
FIG. 4 is a cross-sectional view taken in the direction of the arrow along the line C—C of FIG. 3.
Figure 5:
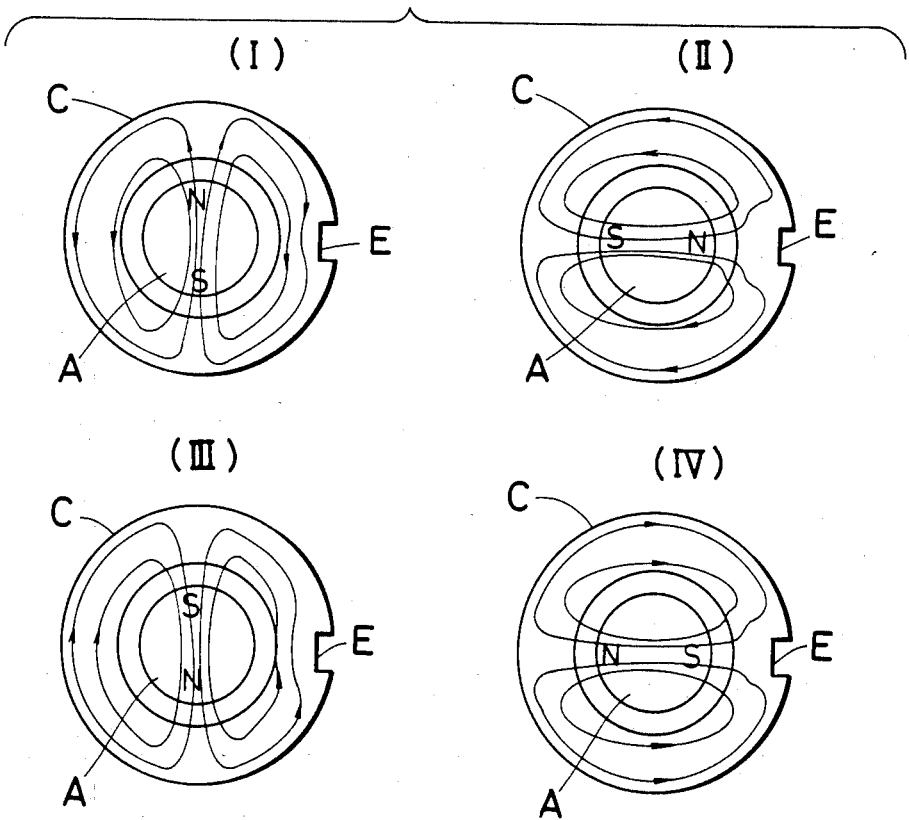

If a sectional area S of the yoke 2 of the invention thus constructed is found in the portion $C_2$—$C_2$ shown in FIG. 7 expansion flat, the area S is obtained by the equation $$S = a \cdot l - b \cdot c$$

and if the groove width $b_2$ of the coolant passageway 1 is 1.1 m/m and other values a, $b_1$, and l are substituted by the aforestated equation, a reduction in the sectional area S can be held down to about 1%. Accordingly, the sectional area of the yoke 2 is reduced by about 1% also in any given longitudinal sectional position along the axis of the yoke because of the spiral arrangement of the coolant passageway 1, but a saturation phenomenon of magnetization of the yoke is not produced and a magnetic path is formed normal, and hence no reduction in motor torque. Also, the sectional area in the direction of the entire periphery of the yoke is evenly and very slightly reduced, so that the distribution of the magnetic flux during rotation of the rotor magnet is rendered symmetric in any phase position of turning angle of the rotor magnet. Further, since the unsymmetric and symmetric distribution of the magnetic flux shown in FIG. 5 is not repeated, the motor is not subjected to cogging and hence no torque ripple is produced.

A detailed description will now be given of an embodiment of the handpiece of the invention shown by way of example with reference to FIGS. 9 and 10 of the accompanying drawings.

FIG. 9 shows a longitudinal section of a grip portion of the handpiece. In FIG. 9 the numeral 3 designates a cylindrical frame, and a micromotor 4 incorporated in the frame 3 comprises a cylindrical stator coil 5, a rotor shaft 7 rotatably journalled in the frame sides by a pair of front and rear bearings 6, a rotor magnet 8 fixed coaxially on the shaft 7, and a cylindrical yoke 2 holding the stator coil 5.

The yoke 2 is fixed to the inner surface of the frame 3. A coolant passageway 1 is formed on the outer periphery of the yoke 2 in a helical manner to wind round the yoke 2 as shown in FIG. 10. A coolant pipe 9 is also formed in the passageway 1 in the range of the rear end 2a to the front end 2b of the yoke 2 and the rear end 9a of the coolant pipe 9 is connected to a coolant supply source (not shown) and the front end 9b is led to the front end side of a handpiece body 10.

As is apparent from the above description, according to this invention, the coolant passageway 1 formed on the outer periphery of the yoke of the brushless micromotor is provided not parallel but spirally to the axis of the yoke. Also, the sectional area of the yoke, irrespective of formation of the passageway, is made approximately definite in any given longitudinal sectional position along the axis of the yoke. As a result, the sectional area of the yoke is not extremely decreased at a partcular point to saturation. Hence, the torque of the micromotor is not decreased, and enlargement of the size of the handpiece can be prevented by the use of a small-sized micromotor. Thus, a handpiece with excellent gripping characteristic and constant turning torque is provided in a form useful for dental treatment.

Having described our invention as related to the embodiment shown in the accompanying drawings, it is our intention that the invention be not limited by any of the details of description unless otherwise specified, but rather may be construed broadly within its spirit and scope as set out in the accompanying claims.

We claim:

1. A medical handpiece having a brushless micromotor incorporated in a body of the handpiece and having a coolant passageway formed on the outer periphery of a cylindrical yoke fixed to the frame of the handpiece body, said handpiece being characterized in that said coolant passageway is formed so as to extend helically around the axis of the yoke from one end to the other end of the yoke.

2. A medical handpiece according to claim 1, wherein said coolant passageway comprises a helical groove having an integral number of times more turns extending from one end to the other end of the yoke.

3. A medical handpiece according to claim 1 or 2, wherein said handpiece is a dental handpiece.

4. A medical handpiece according to claim 1 or 2, wherein a coolant pipe is placed in said coolant passageway.

5. A medical handpiece according to claim 4, wherein said handpiece is a dental handpiece.

* * * * *

UNITED STATES PATENT AND TRADEMARK OFFICE
CERTIFICATE OF CORRECTION

PATENT NO. : 4,568,283
DATED : February 4, 1986
INVENTOR(S) : Toshihiro Hotta et al It is certified that error appears in the above—identified patent and that said Letters Patent is hereby corrected as shown below:

In [75] Inventors: amend "Imazatol Minoru" to

--Minoru Imazato--.

Signed and Sealed this

Tenth Day of June 1986

[SEAL]

Attest:

DONALD J. QUIGG

Attesting Officer

Commissioner of Patents and Trademarks